United States Patent
Pantino

[11] Patent Number: 5,832,918
[45] Date of Patent: Nov. 10, 1998

[54] METHOD OF MAKING A FACE MASK FROM A FACIAL IMPRESSION AND OF GAS DELIVERY

[76] Inventor: Don A. Pantino, 4 Valley Ct., Mount Sinai, N.Y. 11766

[21] Appl. No.: 771,211

[22] Filed: Dec. 20, 1996

[51] Int. Cl.⁶ .......................... A61M 15/00; A61M 16/00; A62B 18/02; A62B 18/08
[52] U.S. Cl. ............................... 128/205.25; 128/200.24; 128/206.21; 128/206.24; 128/207.11
[58] Field of Search .......................... 128/206.21, 206.24, 128/206.26, 206.28, 207.11, 207.13, 200.24, 205.25

[56] References Cited

U.S. PATENT DOCUMENTS

| | | | |
|---|---|---|---|
| 4,437,462 | 3/1984 | Piljay et al. ........................ | 128/207.11 |
| 4,848,334 | 7/1989 | Bellm ................................. | 128/207.11 |
| 5,492,116 | 2/1996 | Scarberry et al. ................. | 128/206.24 |
| 5,592,938 | 1/1997 | Scarberry et al. ................. | 128/206.24 |

*Primary Examiner*—Kimberly L. Asher
*Attorney, Agent, or Firm*—Ward & Olivo; John W. Olivo, Jr.; John F. Ward

[57] ABSTRACT

The present invention relates to improved methods and apparatus for the delivery of respiratory therapy in the treatment of respiratory disorders and abnormalities, such as apnea and other sleep disorders. A qualified professional takes a moulage of a patient's facial skeletal structure and therefrom casts a custom hard shell of the imprinted facial features. Upon the shell hardening, the shell is then lined and further manipulated and a soft gasket interface attached to the mask where the mask interfaces with the patient's face. The contact medium, coupled with the custom hard shell, allows for a vacuum-like seal. A section is then cut and an area sufficient to allow the attachment of the respiratory devices for the supply of air is created. The apparatus is further held in place by means of a strap-like device having one or more contact points upon the present invention. The present disclosure overcomes the prior devices, enhancing seal, comfort effectiveness and patient compliance.

5 Claims, 7 Drawing Sheets

METHOD OF MAKING A FACE MASK FROM A FACIAL IMPRESSION AND OF GAS DELIVERY

BACKGROUND OF THE INVENTION

The present invention is related to improved methods and apparatus by which a patient interfaces with respiratory devices.

FIELD OF INVENTION

The invention relates to respiratory therapy for treatment of sleep apnea, snoring and similar respiratory conditions. In particular, the present invention relates to improved methods and apparatus for patient interfaces and control of respiratory therapy apparatus.

Difficulty of breathing while sleeping often manifests itself as snoring or the more serious obstructive sleep apnea. Snoring is a condition affecting approximately 40% of the adult population, while sleep apnea is believed to affect—at a minimum—approximately 7% of the adult population. The New England Journal of Medicine, in April of 1993, estimated 97 million Americans habitually snore. Of these millions, at least 16 million are thought and known to be afflicted with sleep apnea. Obstructive sleep apnea largely afflicts overweight men, although it can effect men and women of any stature.

Although snoring can occur as a result of a physical anomaly, such as enlarged tonsils, adenoids, or nasal polyps, naming a few, snoring occurs during sleep because the muscles of the upper airway, including the tongue and throat, are relaxed. As a person breathes, the turbulence associated with the passage of air through the respiratory orifices causes a flutter effect on the soft tissues of the upper throat, resulting in the sounds of snoring.

Snoring itself, absent apneic episodes, is destructive. Snoring has direct adverse effects on both the snorer as well as the spouse or mate of the snorer. Restless and intermittent sleep patterns caused by snoring produces daytime irritability for all those within earshot of the snoring. Marital problems resulting from the lack of sleep may have additional ramifications. Relationships may become strained after decisions are made to sleep in separate bedrooms and otherwise avoid partners in situations where the snoring would be troublesome or embarrassing.

Many other sleep related respiratory conditions are caused by a blockage or a partial blockage of the respiratory tract. As blockage of the respiratory passages increase air flow volume is reduced four (4) fold—Hyponea. Long term or severe hyponea in turn results in apnea.

Sleep-induced apnea compounds the problems associated with snoring. Apnea occurs when there is a temporary cessation of breathing, occurring when the airway becomes substantially or totally blocked. A patient suffering from apnea may stop breathing for reoccurring intervals of ten (10) seconds to two (2) minutes or more, in severe cases. Apnea, and the resulting oxygen deprivation, is now known to have severe medical ramifications upon the individual.

There are three (3) forms of sleep apnea. In one form, Central Apnea, airflow is halted due to lack of respiratory effort. But the most common form of sleep apnea, called Obstructive Apnea, arises from a blockage of the oropharyngeal airway, despite persistent breathing effort. The third identified type of apnea is Mixed Apnea, a combination of Central and Obstructive Apnea.

With any form, however, when levels of carbon dioxide increase in the blood and oxygen levels decrease—resulting from the cessation of breathing—the brain triggers normal respiration to resume, usually accompanied by gasping and wheezing. Quite often the snorer is momentarily awakened, concluding the apneic episode, only to fall back to sleep and repeat the cycle. In other cases the patient can suffer from a plethora of problems stemming from the reduction in blood oxygen levels such as high blood pressure, low energy levels, strokes or cardiac arrest and in the most severe cases death.

Besides the physical and physiological effects associated with snoring and apnea, such individuals are likely to suffer additional personal and economic harms. For instance sleep apnea may cause a patient to have difficulty functioning in a normal manner during the day because of insufficient Rapid Eye Movement (REM) sleep as a result of the patient awakening in order to overcome airway blockage. As a consequence of the numerous nightly sleep disruptions (arousals), that the snorer may not even be consciously aware of, those with sleep apnea may experience severe daytime drowsiness that leads to accidents and injuries. Chronic sleepiness will also translate into economic harm through poor job performance as the individual may be late to work, dose off, have a short attention span, be easily distracted and usually give less attention to detail. Furthermore, individuals with sleep apnea tend to take more sick leave.

Accordingly, the medical profession and related industries have begun to recognize the paramount importance of developing new and innovative techniques to reduce and eliminate snoring and apnea. As a result, to determine the actual cause and severity of the snoring or apnea, it has become necessary to first examine the patient before prescribing any remedial measure. For example, if a structural anomaly is discovered to cause the breathing disorder, then surgery may be recommended. Although such severe steps such as surgery can be taken to alleviate snoring and the more serious condition of sleep apnea—like a tracheostomy, Laser Assisted Uvulopalatopharyngoplasty (LAUP) and Uvulopalatopharyngoplasty (UPPP)—to ensure adequate ventilation; it is desirable to provide a treatment that is non-surgical. For many patients, surgery is not needed and should be avoided as non-evasive remedies are preferred. In response, and as an alternative to surgery, behavior modification such as weight loss, positional therapy and oral appliance therapy have been developed as alternative non-evasive treatments.

The gold standard to date for the treatment of sleep apnea is Continuous Positive Airway Pressure (CPAP). When used as prescribed it has the potential for 100% effectiveness in treating sleep disordered breathing problems. The problem with CPAP, and other similar respiratory devices, has been patient compliance. Recent studies of CPAP operating "chips" (computer monitoring devices) indicate poor patient compliance. Studies have indicated that only 40–60% of the patients use the respective device on a nightly basis. Further, of that percentage, a majority fail to use the apparatus for a sufficient time to achieve any true therapeutic results. The predominant factor cited by the patients surveyed is dissatisfaction with the patient/apparatus respiratory interface, i.e. the nasal cannulars or facial mask.

The dissatisfaction largely results from the "one size fits all" approach the manufactures have taken in addressing the patient/machine interface. Because most respiratory therapy is long term, the need for comfortable, durable interfaces has, as of date, not yet been effectively and efficiently addressed.

Many approaches have been taken in addressing the problem of snoring and sleep apnea, ranging from simple weight loss, which has been shown to somewhat reduce snoring and apneic episodes in overweight persons, to the use of oral appliances, to the use of CPAP applied through the respiratory orifices, to radical surgical approaches such as tracheostomy, LAUP and UPPP.

Currently, there are a number of therapeutic apparatus that avoid the need for surgery.

Oral Appliances

Oral appliances are worn in the mouth during sleep to prevent the tongue and oral pharengial tissues from collapsing and obstruction the airway. According to the American Sleep Disorders Association (ASDA), Oral Appliance Therapy (OAT) is appropriate for benign snoring and mild to moderate apnea. Thus, oral devices are limited in their application and may be uncomfortable for the patient.

Nasal Apparatuses

U.S. Pat. No. 4,944,310 consists of an apparatus having a flexible tubing portion with a standard cavity nose piece shaped for insertion into a patient's nose and adapted to the patient's face. The shortcomings with this device are obvious—the device is inserted into the patient's nose—and contains a high degree of discomfort. Additionally, there is leakage of air proximally resulting from the inefficient and ineffective seals between the device and the patient. Further, nasal apparatuses invade the patient's nose to such a degree that it is obvious to both the patient and an observer of such usage. Thus, theses devices have clear limitations and drawbacks.

Masks

Many sleep apnea patients are now prescribed CPAP, Direct Positive Airway Pressure (DPAP), Intermittent Positive Airway Pressure (IPAP) and Bi-level Positive Airway Pressure (BAP.) devices. In the use of such respiratory devices a sufficient positive pressure is applied to the patient's airway preventing collapse or blockage. Typically, said pressure is within specific ranges, from three (3) to twenty (20) cm of $O_2$ dependant upon the patient's needs and amount of leakage from the interface apparatus. A description of CPAP in use with nasal masks and like devices can be obtained from U.S. Pat. No. 5,243,971.

All prior nasal and facial masks fail to disclose devices that effectively address or remedy patient discomfort and air leakage. Initial attempts to reduce the loss of air involve attaching the masks to the patient's head with multiple straps. In another attempt to redress the losses indicative of the prior apparatuses, some prior disclosures increase: the number of point/strap attachments; tension with which the mask is held in place; and air pressure from the respective delivery device, i.e. CPAP, in a futile attempt to effect an more efficient seal. As a direct result, the mask becomes too tight and the patient develops sore contact spots, is uncomfortable and therefore discouraged from using the prescribed remedy. In addition, even with these modifications air is still lost. Further, none of the apparatuses address the loss of vision or cumbersome nature of such apparatuses.

Some proximate causes of these shortcomings are: 1) the varying facial and skeletal morphology of the patients, and 2) the products attempting to redress these problems in a "one size fits all" scenario. All the prior mask devices comprise a soft medium that fails to maintain structural integrity. Accordingly, the disclosures fails to adequately address or remedy that for which it was intended, improved patient ventilation.

For example, U.S. Pat. No. 5,560,354 discloses a mask for use in ventilation. The mask comprises a curved portion connected to a supply of pressurized air, a shaped cushion extending from the body portion being shaped to form a rolled edge seal circumscribing a region around respiratory orifice. The cushion fails to provide structural integrity requiring the mask to be tightly worn in a maligned attempt to compensate for poor fit and inadequate seal. This device is ineffective because of the inadequate seal—and inherent loss of air—in addition to the multiple attachment points leading to the device being cumbersome and uncomfortable.

U.S. Pat. No. 4,919,128 discloses a device that includes a sealing means that seals the external part of the nares without cannulating the nostril. However, as earlier addresses, this device fails to redress the loss of air while attempting to increase patient comfort and therein is self defeating, as the straps must be tightened to compensate for the inefficient seal.

U.S. Pat. No. 5,517,986 relates to a multi-point mask. The device provides cap-like headgear that utilizes two-point and four-point connections to and between the mask and patient's face. This device is limited in being extremely cumbersome to use, still requiring a "tight" fit and the increased pressure to attempt to overcome poor facial adaptation. Thus, the device fails to effectively address patient comfort and compliance, failing to adequately redress the problem poor facial adaptation and leakage. This device fails to disclose devices to maintain the structural integrity necessary for comfort and seal.

U.S. Pat. Nos. 5,243,971; 5,537,994, and '354 above cited, all share the same common shortcomings. Foremost, they all restrict the patient's vision and movement because the devices extend well off of the patient's face and all have cumbersome manners for respiratory apparatus attachment protruding therefrom. Further, all require multiple points of attachment. Finally, and most limiting, the devices are generally comprised of soft pliable mediums that fail to maintain anatomical and structural integrity. This lack of structural integrity results in the loss of air, patient discomfort, and therein greatly decreases patient compliance. Most of the resulting problems stemming from pressure, patient pressure points and soreness associated therewith are proximally caused by the prior devices attempting to compensate for their lack of structural integrity stemming from their poor facial and skeletal adaptation and fit.

In sum, none of the products effectively address the shortcomings of the prior devices, attributable to the masks being universally comprised of soft pliable compositions therein failing to maintain a set contact point(s) by which the mask can be affixed.

These and other objects and advantages of the present invention will become apparent from the following descriptions, accompanying drawings, and claims.

SUMMARY OF THE INVENTION

The present invention is a vast improvement on presently available products as it addresses patient comfort, adequate patient/apparatus interface seal, and therein patient compliance. The present disclosure embodies a device that is derived from a custom mold and is comprised of materials that allow it to maintain a hard shell able to maintain structural integrity that in turn allows for novel manners of retention and attachment to the patient's face.

A patient in need of respiratory assistance has a facial moulage, or like means, taken whereby a working model of the respiratory orifices and surrounding structures is created. The model is then prepared for the construction of an anatomically correct custom shell using a preferred means by one skilled in the art. The model is then adjusted to make allowances for adequate airspace, allowance(s) for the attachment of an air supply, and a means of attachment by which a strap(s) may be attached or positioned. Finally, a soft gasket interface is attached to the area of "shell-skin" interface. Thus, the aforementioned methods leads to the custom creation of an anatomically correct skeletally supported patient mask for apparatus interface.

The apparatus is then fitted upon the patient for final adjustments. Following which the patient can use the apparatus with the prescribed respiratory device.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWING FIGURES

DETAILED DESCRIPTION OF THE PREFERRED EMBODIMENTS

Figure 1:
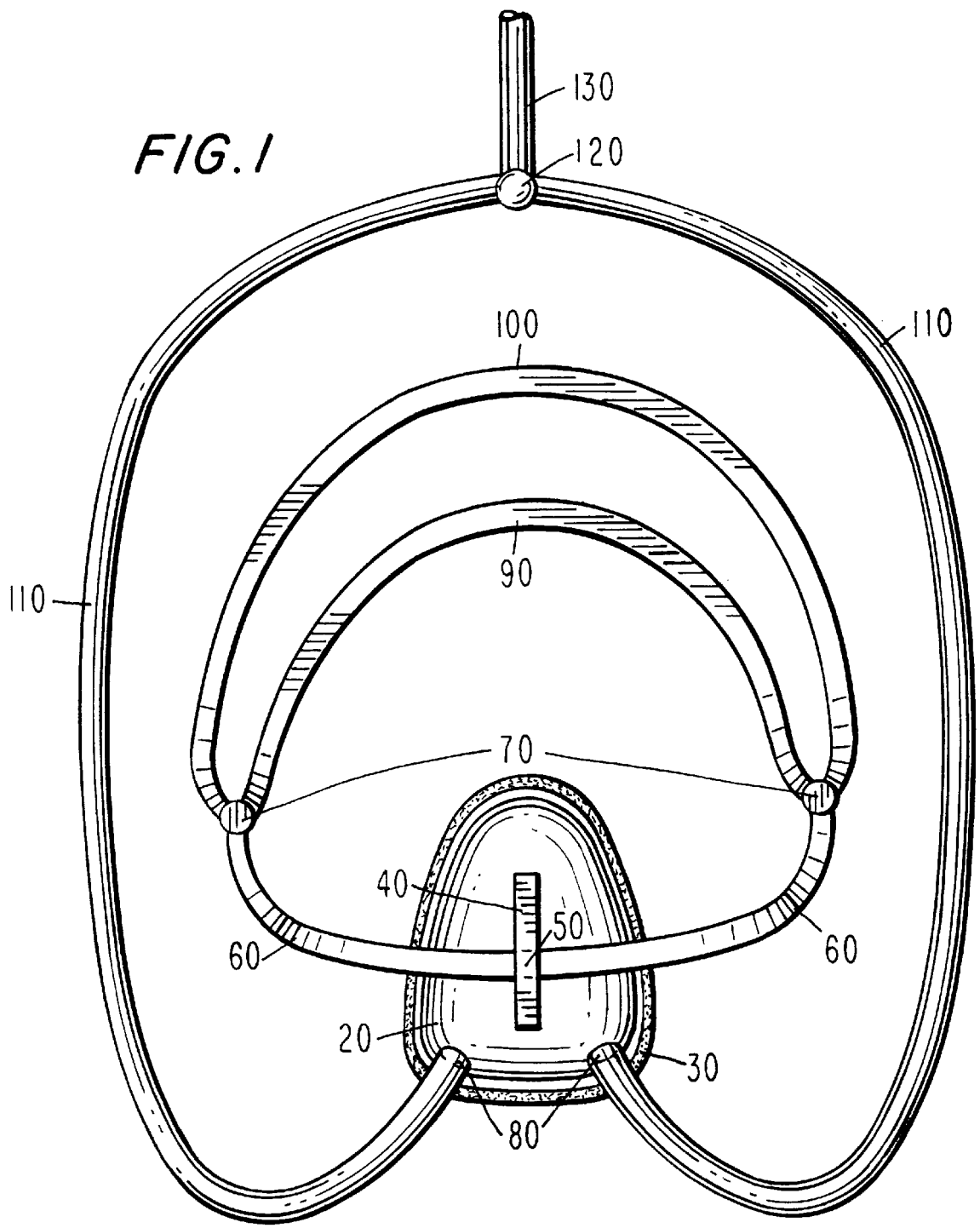
FIG. 1 Depicts a frontal view of the apparatus.

FIG. 1 illustrates a frontal view of a custom hard shell mask according to the teachings of the present invention. As shown in FIG. 1, the mask 10 is provided for fitting over a patient's respiratory orifice. The particular mask 10 shown in FIG. 1 is illustrative only, and any other mask shapes may be used without departing from the intended scope of the present invention. For example, the mask 10 may fit over the patient's nose and mouth together, or mouth or nose alone. As shown in FIG. 1, mask 10 contains a custom formed hard shell 20 that has a soft gasket interface layer 30 that is in contact with the patient's facial epidermal tissue. The mask 10 contains an adjustable point of attachment 50 that can be attached anywhere upon the mask 10 such that the custom mask 10 may be custom fitted the patient. A preferred location for such points of attachment 50 would be area 40 located on the exterior of the shell 20, vertically transecting the shell 20, extending from short of the bottom to short of the top of shell 20.

The hard shell 20 is comprised of materials that are of a hard, rigid, durable nature capable of maintaining the mask's 10 structural integrity while in use and for an extended period of time. Thus, the material will allow the custom mask 10 to be used over the period of many months.

Attached to the hard shell's 20 point of attachment 50 may be a strap 60 or strap-like member. The strap 60 extends from the mask 10 to the patient's cranium along the Tragal line to a point 70 where it separates from one member 60 into two members 90, 100. The separation occurs prior to the Tragal line reaching the ear's canal. At the point of separation the two resulting members 90, 100 diverge in angulated directions. The member 90 proceeding up the scalp to the upper cranium encompasses the cranium's circumference and reattaches to the opposite side from which it was separated. In turn the member proceeding towards the lower cranium 100 where the spine enters the cranium encompasses that portion of the cranium's circumference and reattaches opposite the side from which it was separated 70. The angle at the points of separation is determinative upon, and can be altered in accordance with, the size of the patient's cranium. Accordingly, the lengths of the straps 90, 100 can also be altered according to the size of the patient's cranium. Furthermore, the strap 60 may be comprised of either nylon, elastic or combination thereof. The cranial straps 90, 100 may be comprised of a nylon-like material having a mechanism whereby the cranial straps 90, 100 may be adjusted to custom fit the patient's cranium. The hard shell's 20 point of attachment 50, coupled with the ability to be located at a variation of positions upon the hard shell 20, allows the strap 60 to diverge into two members 90, 100 that in turn permit the custom mask 10 to maintain a custom tailored fixed position upon the patient's face.

The custom hard shell mask 10 receives pressurized air delivered via an air passage 80 attached to a hose-like member 110. The pressure of the air delivered by apparatus depends upon the severity of the breathing disorder being treated. The more severe the disorder, the greater the pressure must be. Various apparatuses for delivering air at constant or varying pressures may be used.

Accordingly, gas mediums are supplied to the custom hard shell mask 10 by ways of opening(s) 80 in the shell 20. The opening(s) 80 are located on the shell 20 in accordance with the needs, skeletal and anatomical structures of the patient. Attached to the opening(s) 80 are tubes 110, or hose-like members, capable of containing and conveying pressurized mediums within. The tubes 110 then circumnavigate the patient's cranium and converge at a point where they form, via an appropriate means of attachment 120, a singular tube 130, or hose-like member, conveying the pressurized medium therein from an apparatus to the mask 10.

In summary, a custom hard shell mask 10 is provided wherein it is connected to an apparatus capable of supplying pressurized ventilation.

Figure 2:
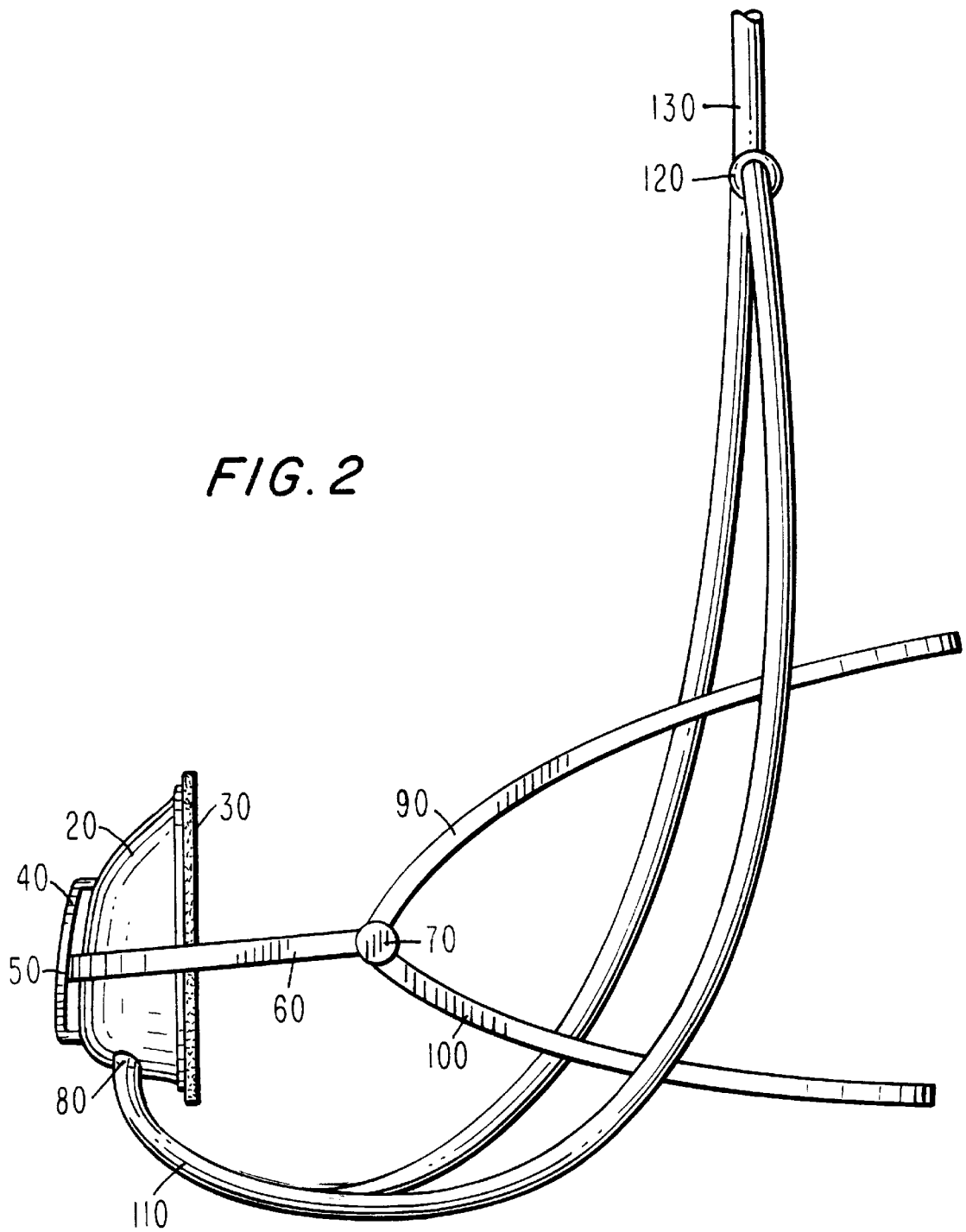
FIG. 2 Depicts a profile of the apparatus.

FIG. 2 illustrates a side profile view of a custom hard shell mask 10 according to the teachings of the present invention. As shown in FIG. 2, the mask 10 is provided for fitting over a patient's respiratory orifice and surrounding areas. The particular mask 10 shown in FIG. 2 is illustrative only, and any other mask shapes may be used without departing from the intended scope of the present invention. As shown in FIG. 2, mask 10 contains a custom formed hard shell 20 that has a soft gasket interface layer 30 that is to contact the patient's epidermis. The soft gasket interface layer 30 extends and is attached, by an appropriate means, whereby it will remain attached to the shell 20 for the duration of its use. The soft gasket interface layer 30 should be of a material possessing the qualities of: limited epidermal abrasiveness; pliable, in conforming to the unique anatomical and skeletal attributes of the patients face; dense enough to form a vacuum-like seal, when placed upon the face coupled with the use of retention straps 60, 90, 100, and durable enough to maintain the aforementioned physical attributes for an extended period of time.

The mask 10 encompassing a custom hard shell 20 and soft gasket interface layer 30 is held in place by a strap 60 that diverges into two straps 90, 100. The strap 60 is attached to the shell 20. The point of attachment 50 is located on a vertical plane 40 that permits the appropriate positioning for the strap 60 on the shell's 20 point of attachment 50, dependent upon the anatomical attributes of the patient. Therein, the point of attachment 50 is demonstrative only. Accordingly, dependant upon the patient's anatomical and skeletal attributes, there may be multiple points of attachment, whereby the same custom fitting effect is achieved. The point of attachment 50 may encompass a loop or other means by which the straps may pass freely through, or alternatively, may be affixed, attached, or adhered permanently or for the duration of the custom mask's 10 use.

The delivery of pressurized air is accomplished by a hose 130 or like delivery means that is further separated into two like mediums 110 that in turn are attached to the shell at point 80 most conducive to the delivery of the pressurized air to the patient.

FIG. 2 further depicts the attachment of the hoses 110 to the strap 60, whereby they follow or are attached to the strap 90 and proceed toward the posterior cranial lobe. Upon reaching a desired location at said lobe, the hoses 110 converge into a singular hose 130 that then leads to the respiratory apparatus.

Figure 3:
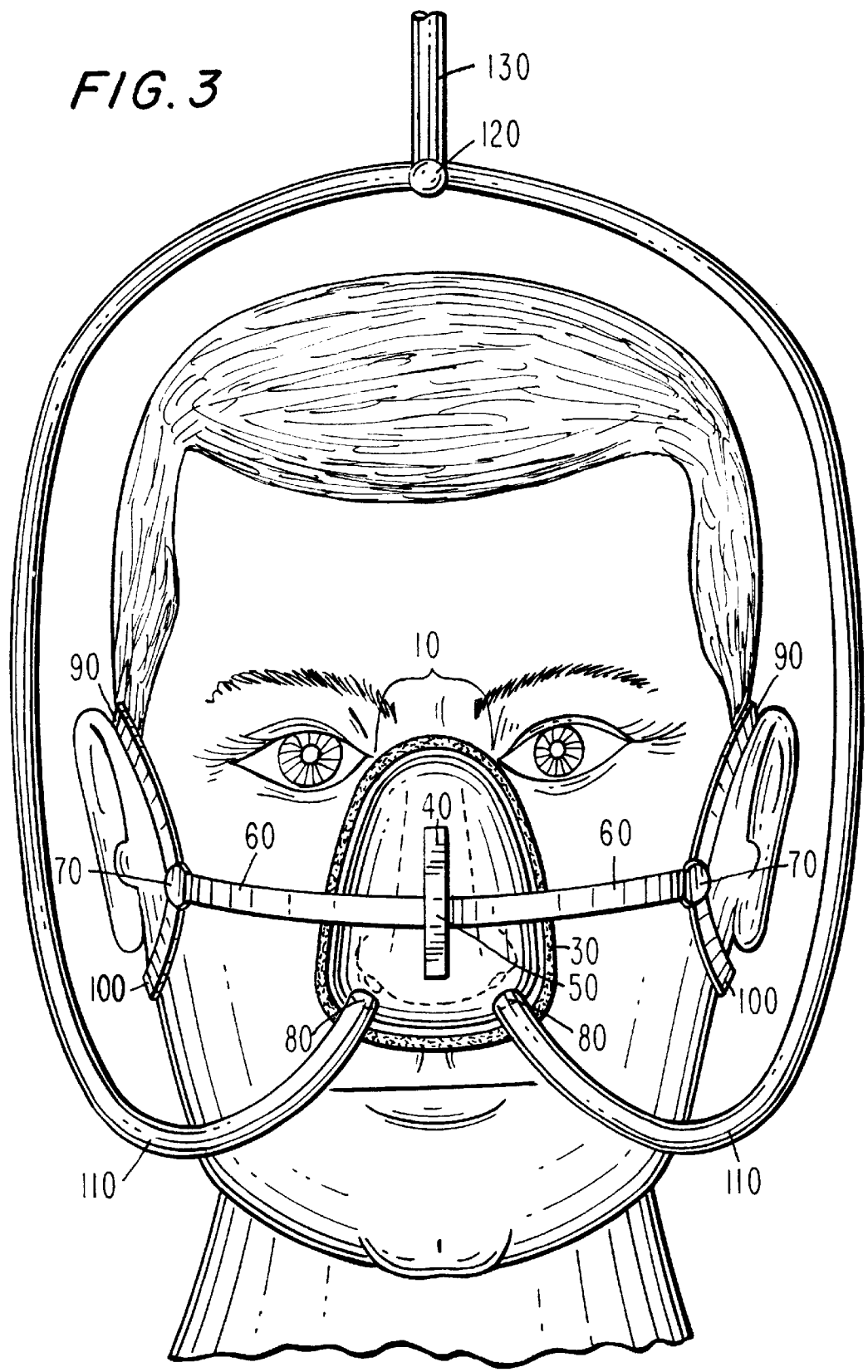
FIG. 3 Depicts a frontal view of the apparatus while in use on the patient.

FIG. 3 illustrates a frontal view of a custom hard shell mask according to the teachings of the present invention. As shown in FIG. 3, the mask 30 is provided for fitting over a patient's respiratory orifice and surrounding area. The particular mask 10 shown in FIG. 3 is illustrative only, and any other mask shapes, strap or hose combination, as disclosed herein, and may be used without departing from the intended scope of the present invention.

FIG. 3 illustrates one manner by which the present disclosure may be worn by a patient. The custom mask 10, comprising a custom molded hard shell 20 and a soft gasket interface 30, is held upon the patients face via a retention strap 60 that "runs along or close to" the Tragal line, diverging 70 prior to reaching the ear's canal into two straps 90, 100. The respective strap 90, 100 circumnavigate the cranium and reattach on the opposite side from which they began 70. As disclosed in the description of FIG. 1, these straps 60, 90, 100 may be comprised of, but need not be limited to, that which was disclosed.

The delivery of air is via a respiratory device capable of delivering pressurized air to the patient's mask 10. This delivery is accomplished by the attachment of a hose 130 to the apparatus and the hose 130 diverging into two hoses 110 that in turn are attached to the mask's 10 hard shell 20 in a location that is correct for the patient's needs.

Figure 4:
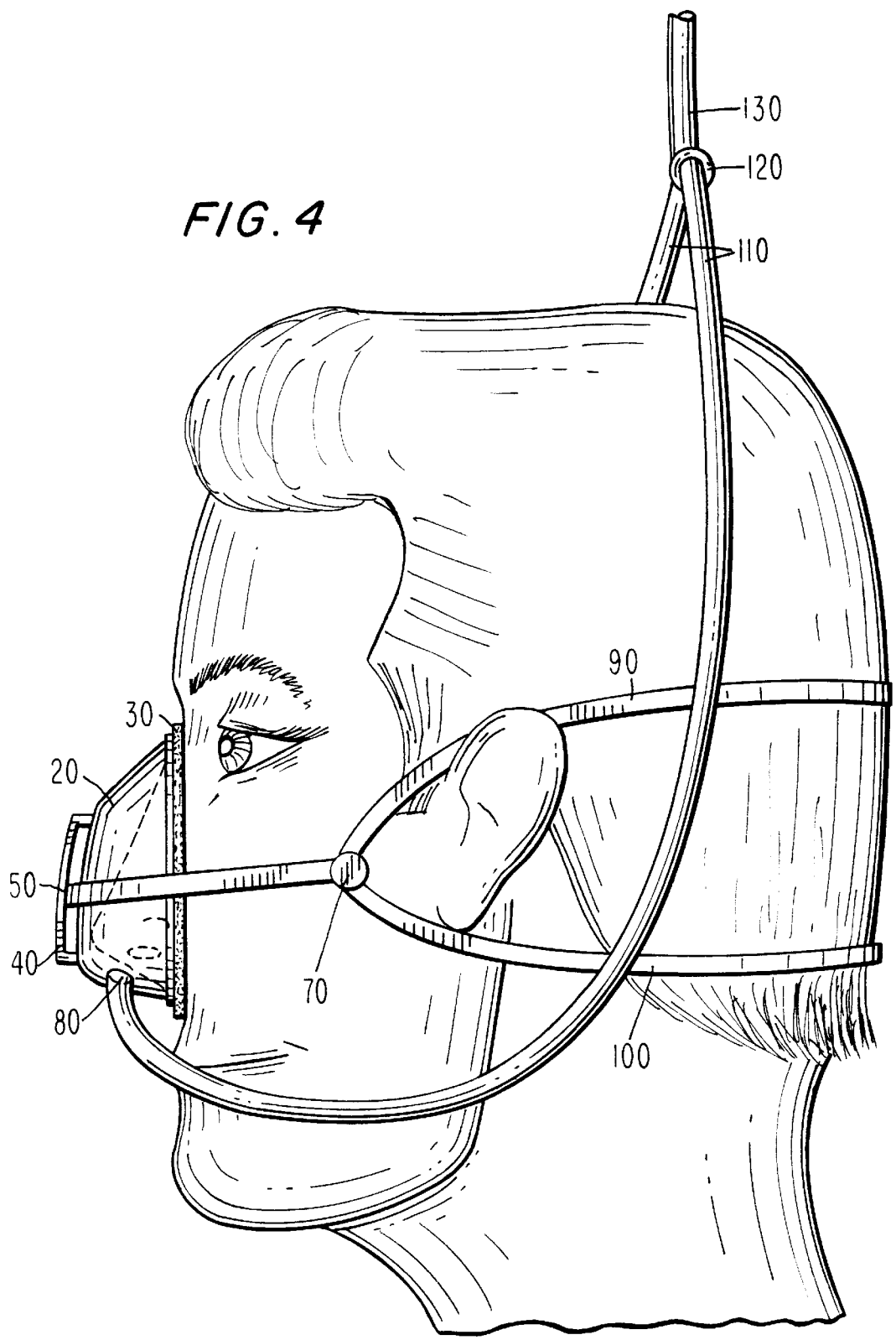
FIG. 4 Depicts a profile of the apparatus while in use on the patient.

FIG. 4 illustrates a profile view of a custom fitted and molded mask according to the teachings of the present invention. As shown in FIG. 4, the mask 10 is provided for fitting over a patient's respiratory orifice and surrounding area. The particular mask 10 shown in FIG. 4 is illustrative only, and any other mask shapes may be used without departing from the intended scope of the present invention.

FIG. 4 depicts a nasal mask 10, comprised of a custom hard shell 20 coupled with a soft gasket interface layer 30, covering a patient's nose and some of the surrounding tissue. The custom hard shelled mask 10 is held in place by a strap 60 that diverges into two straps 90, 100 before reaching the ear. The strap 60 is demonstratively attached to the mask 10 at area 40 by means of a point of attachment 50. The area of attachment 40 is upon the vertical axis of the shell 20. The point of attachment 50 may consist of any variation of a loop or other means that would allow for the strap's 60 free movement, or not, therethrough, while maintaining the mask's 10 custom fitted fixed position upon the patient's face. Alternatively, the point(s) of attachment 50 may affix a strap 60, comprised of an elastic-like material, to single or multiple points 50 on the mask 10.

Air delivery to the custom formed hard shell 20 mask 10 may, in one embodiment, be accomplished through a hose-like member 130 being attached to an apparatus capable of pressurized air delivery. Wherein, said hose 130 attaches to strap 90 and therein continues—down the left or right side of the cranium—in conjunction with strap 90 to the strap's 90 point of convergence with the other cranial strap 100. At the point of said convergence, hose 130 is then affixed to the strap 60 and then proceeds towards the oral orifice on the Tragal line. Upon gaining close proximity to the oral or nasal orifice the hose 130 diverges into separate hoses 110 that in turn are attached to the mask 10 at the ventilatory openings 80. Alternatively, the hose 130 could proceed and attach directly to the ventilatory opening(s) 80. The point of ventilatory passage 80 is located such that the air's delivery will be optimized in accordance with the patient's needs.

Figure 5:
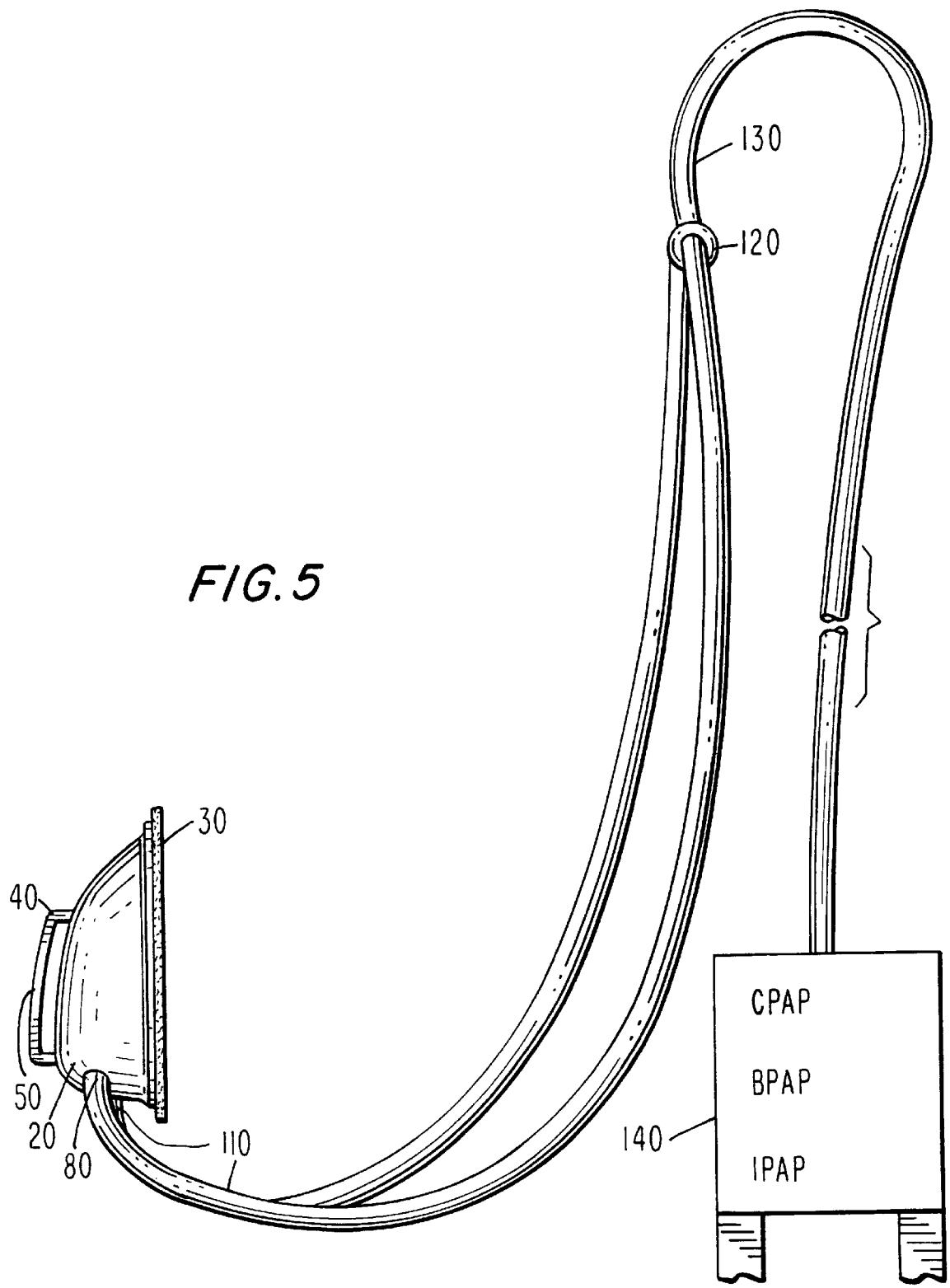
FIG. 5 Depicts a device with manner of attachment to a respiratory device.
Figure 6A:
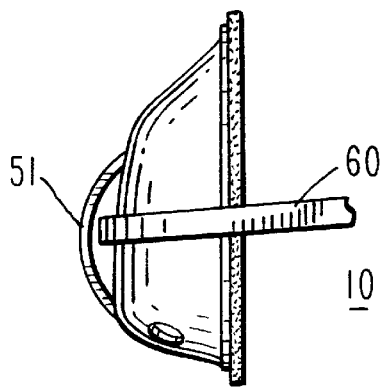
FIG. 6 Depicts manners of strap attachment to the mask's shell.
Figure 6B:
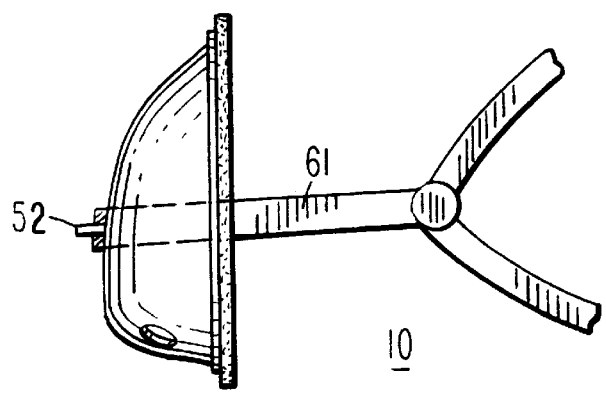
Figure 6C:
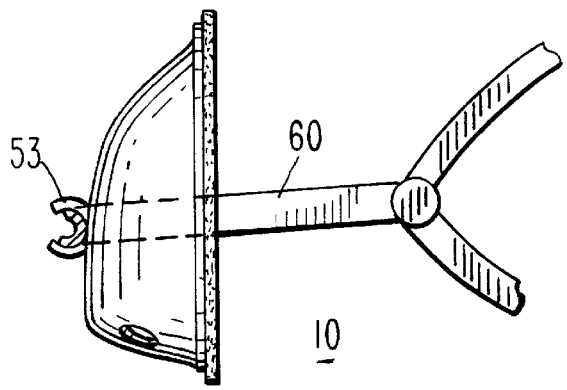
Figure 6D:
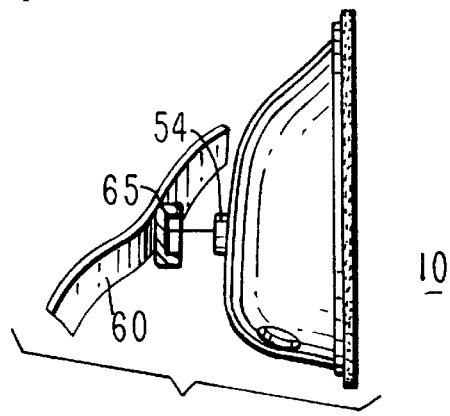

The particular mask 10 shown in FIG. 5 is illustrative only, and any other mask shapes, hose 130, 120, 110 and strap 60, 70, 90, 110 combinations, may be used without departing from the intended scope of the present invention.

FIG. 5 illustrates a profile view of a custom formed hard shelled mask 10 whereby the mask 10 is attached 80, 110, 120, 130 to an apparatus 140 capable of delivering pressurized air. Accordingly, the mask 10 is provided for custom fitting (custom hard shell 20, soft gasket interface 30), and attachment to (strap 60, 70, 90, 110 and point of attachment (s) 40, 50), a patient's respiratory orifice. A respiratory apparatus is attached to a hose-like structure 130 that in turn may diverge 120 into two separate hoses 110 and is attached to the mask's 10 shell 20 at a point conducive to said air's delivery 80. On the shell 20 there is a vertical area 40 that transcets the vertical axis of the shell's 20 exterior, upon which a means for strap attachment 50 is located.

FIG. 6 depicts manners 50 through which straps 60 or other retentions means may pass or be attached to a mask 10. Drawing (a) depicts a circular means 51 by which the strap 60 may be retained. Drawing (b) depicts a peg 52 upon which an elastic strap 61 is permanently attached and becomes non-elastic at the point of angulated divergence. Drawing (c) discloses a peg-like means 53 upon which a strap 60 with a means for attachment may be placed, and pass freely thereupon. Drawing (d) discloses a snap-like manner 54 upon which a strap 60 with a like means for attachment 65 may be placed upon an elastic strap.

Figure 7:
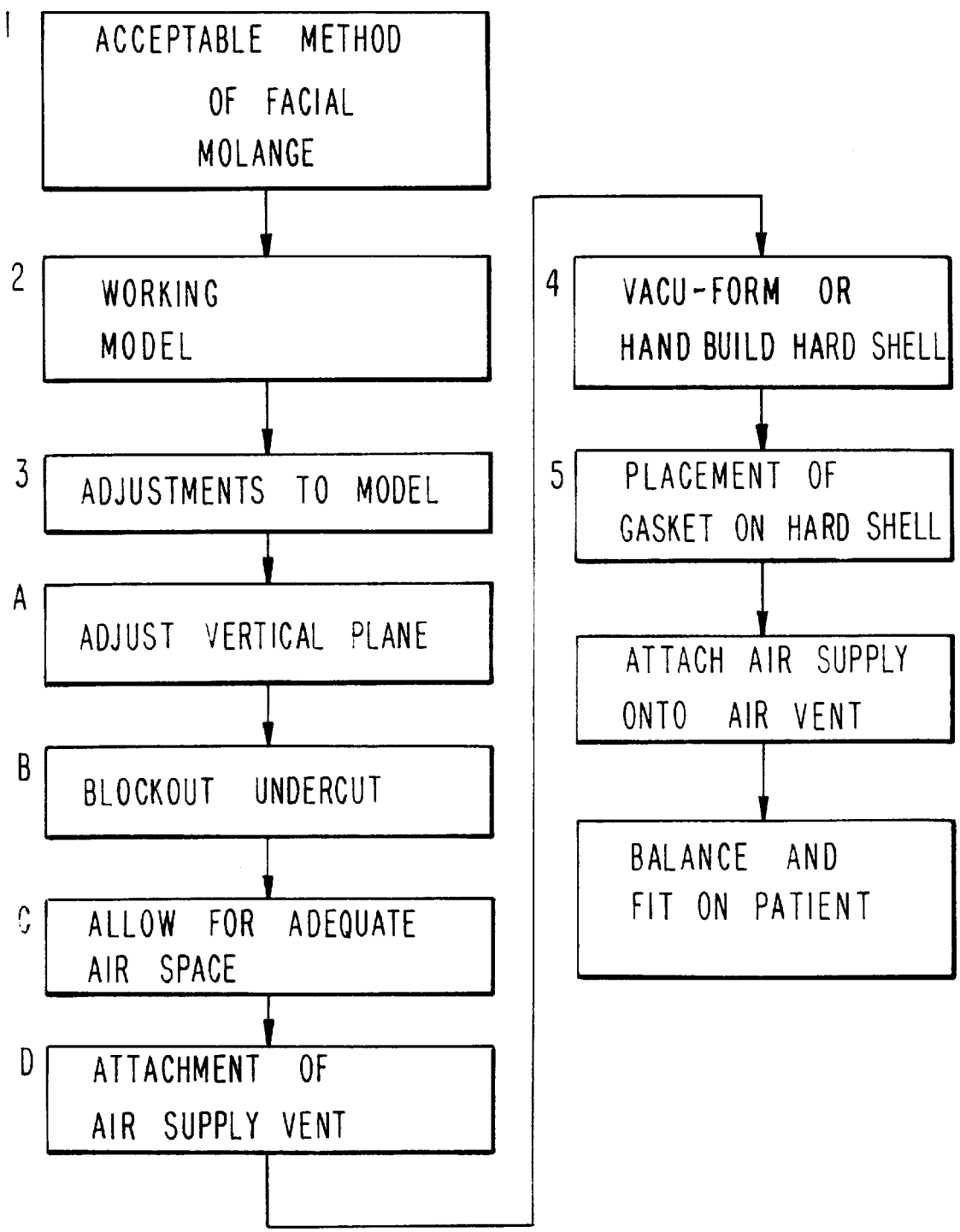
FIG. 7 Represents a manner by which the apparatus is created.

FIG. 7 illustrates a flow chart according to the teachings of the present invention. The flow chart as provided is illustrative only, and means may be substituted without departing from the intended scope of the present invention.

The chart depicts a method whereby a facial impression is taken of a patient's respiratory orifice and skeletal support means. The impression must be of a nature and quality whereby an accurate model of said orifices and surrounding area is created therefrom. Then the resulting model is further manipulated in expanding upon the areas surrounding the respiratory orifices. Next, the model is then covered by a medium that fully envelopes the model. In turn the medium forms a custom shell that encompass the area of the impression. The medium may be applied, conformed, molded or fabricated in any means whereby the resulting shell will be a rigid hard surface. The custom hard shell is then altered, or cut, to permit the passage of air from within the shell to the area outside the shell. The alterations are located in a position that allows for attachment of delivery hoses of pressurized air. Then, the shell is adjusted for attachment and retention upon the patient's face. Accordingly, a soft gasket interface is then placed upon the shell's "edge" that is in contact with a patient's face.

Finally, the completed custom hard shell encompasses a mask that is then adjusted by a professional while on the patient's face via single or multiple attachment points.

Although the present invention has been described in detail, it should be understood that various modifications, substitutions, or alterations can be made without departing from the intended scope as defined by the appended claims.

What I claim is:

1. A method for treating respiratory disorders that requires user interface with devices capable of supplying pressurized gases by means of a device that is adapted to form a seal with a user's face, said method comprising the steps of:

taking a facial impression of a user's respiratory orifice(s) and surrounding area;

creating an accurate representative model of said orifice(s) and area;

manipulating said model to expand upon the area surrounding said orifice(s);

covering said manipulated model by a medium, which then forms a custom surface encompassing said model;

altering said surface such that upon placement on a user's face from which the impression was taken, air will be permitted to pass between said orifice(s) and the area outside the area encompassed by said surface;

adjusting said surface for attachment to a user's face;

placing a soft gasket interface upon said surface's area that would other wise be in contact with a face from which said facial impression was taken; and attaching said model to the user's face during sleep.

2. A method according to claim 1 wherein said expansion allows for a space by which a gaseous medium may surround said respiratory orifice(s).

3. A method according to claim 1 wherein said medium is capable of forming a hard or rigid, durable structure able to maintain structural integrity.

4. A method according to claim 1 wherein said surface alteration may allow for the encompassing member's attachment to a ventilation or respiratory apparatus means by means of an opening that may be cut, carved or molded into said encompassing member with further adaptation allowing for temporary or permanent attachment to said ventilation or respiratory apparatus.

5. A method according to claim 1 wherein said soft gasket interface is of a composition that possesses the physical attributes or is similar to that of neoprene or foam, such that a vacuum-like seal is created when said medium is coupled with said encompassing member and placed on the face of the user.

* * * * *